(12) United States Patent  
Labella

(10) Patent No.: US 12,419,642 B1
(45) Date of Patent: Sep. 23, 2025

(54) HEMORRHOID BANDER AND METHOD OF USE THEREOF

(71) Applicant: LaBella Health Care LLC, Milford, OH (US)

(72) Inventor: Gennaro Labella, Milford, OH (US)

(73) Assignee: LABELLA HEALTH CARE LLC, Milford, OH (US)

( * ) Notice: Subject to any disclaimer, the term of this patent is extended or adjusted under 35 U.S.C. 154(b) by 0 days.

(21) Appl. No.: 18/809,183

(22) Filed: Aug. 19, 2024

(51) Int. Cl.
*A61B 17/00* (2006.01)
*A61B 17/12* (2006.01)

(52) U.S. Cl.
CPC ............ *A61B 17/12009* (2013.01); *A61B 2017/00398* (2013.01); *A61B 2017/0042* (2013.01); *A61B 2017/00477* (2013.01); *A61B 2017/00544* (2013.01); *A61B 2017/00561* (2013.01); *A61B 2017/00734* (2013.01); *A61B 2017/00862* (2013.01); *A61B 2017/12018* (2013.01)

(58) Field of Classification Search
CPC A61B 2017/12018; A61B 2017/00747; A61B 2017/00761; A61B 2017/320012; A61B 2017/320024; A61B 2017/320028; A61B 2017/320032; A61B 17/32002; A61B 2017/12004; A61B 17/12; A61B 17/12009
See application file for complete search history.

(56) References Cited

U.S. PATENT DOCUMENTS

| | | | |
|---|---|---|---|
| 3,760,810 A | 9/1973 | Van Hoorn | |
| 5,464,412 A | 11/1995 | Budding | |
| 5,741,273 A | 4/1998 | O'Regan | |
| 6,436,108 B1 * | 8/2002 | Mears | A61B 17/12013 606/139 |
| 6,974,466 B2 | 12/2005 | Ahmed et al. | |
| 9,101,360 B2 | 8/2015 | Chotenovsky et al. | |
| 9,232,947 B2 | 1/2016 | Brenner et al. | |

(Continued)

FOREIGN PATENT DOCUMENTS

| | | |
|---|---|---|
| WO | 1999065400 A1 | 12/1999 |
| WO | 2006136053 A1 | 12/2006 |

(Continued)

OTHER PUBLICATIONS

US 11,701,122 B2, 07/2023, Basu et al. (withdrawn)

*Primary Examiner* — Majid Jamialahmadi
(74) *Attorney, Agent, or Firm* — ArentFox Schiff LLP

(57) ABSTRACT

Apparatuses and methods of the present disclosure generally relate to a hemorrhoid bander including a housing, an actuation system positioned within the housing, a power source positioned within the housing, the power source configured to provide power to the actuation system, an outer shaft defining a hollow passageway, and an inner shaft positioned within the hollow passageway of the outer shaft. The inner shaft includes a distal end having an opening, a hollow passageway, and a proximal end. The inner shaft and outer shaft are relatively movable between a first position and a second position. The actuation system is coupled to an end of a first one of the inner shaft or the outer shaft and configured to move the inner shaft and outer shaft between the first position and the second position; a second one of the inner shaft and the outer shaft is fixedly coupled to the housing.

24 Claims, 11 Drawing Sheets

(56) References Cited

U.S. PATENT DOCUMENTS

| | | | |
|---|---|---|---|
| 9,622,750 B2 | 4/2017 | Chotenovsky et al. | |
| 9,693,778 B2 | 7/2017 | Kamler | |
| 9,987,437 B2 | 6/2018 | Markle et al. | |
| 10,463,375 B2 | 11/2019 | Taffa et al. | |
| 10,660,644 B2 | 5/2020 | Robbins et al. | |
| 10,744,274 B2 | 8/2020 | Markle et al. | |
| 11,123,076 B2 | 9/2021 | Nguyenba et al. | |
| 11,484,317 B2 | 11/2022 | Saenz Villalobos et al. | |
| 2006/0200176 A1* | 9/2006 | Matsuno | A61B 1/00089 606/140 |
| 2006/0259042 A1 | 11/2006 | Hassanien | |
| 2010/0063517 A1* | 3/2010 | Cleator | A61B 17/12 606/140 |
| 2010/0130857 A1 | 5/2010 | Szinicz | |
| 2010/0234859 A1 | 9/2010 | Bastia | |
| 2010/0234949 A1 | 9/2010 | Bastia | |
| 2011/0077666 A1* | 3/2011 | McCahon | A61B 17/12013 606/139 |
| 2015/0272587 A1 | 10/2015 | Barclay | |
| 2016/0008000 A1 | 1/2016 | Su et al. | |
| 2016/0242787 A1 | 8/2016 | Nayar | |
| 2019/0099186 A1 | 4/2019 | Piskun | |
| 2020/0146682 A1 | 5/2020 | Chotenovsky et al. | |
| 2020/0237205 A1 | 7/2020 | Ungerstedt | |
| 2021/0007749 A1 | 1/2021 | Basu et al. | |
| 2021/0022596 A1 | 1/2021 | Keenan et al. | |
| 2021/0022746 A1 | 1/2021 | Smith et al. | |
| 2021/0030424 A1 | 2/2021 | Bhowmick et al. | |
| 2021/0282783 A1 | 9/2021 | Moore et al. | |
| 2022/0160365 A1 | 5/2022 | Shah et al. | |
| 2022/0346797 A1* | 11/2022 | Tal | A61B 17/12013 |
| 2023/0157695 A1 | 5/2023 | Pei et al. | |
| 2024/0285313 A1* | 8/2024 | Jeon | A61H 9/0028 |

FOREIGN PATENT DOCUMENTS

| | | |
|---|---|---|
| WO | 2007079674 B1 | 8/2007 |
| WO | 2017089982 A1 | 6/2017 |
| WO | 2020164409 A1 | 8/2020 |
| WO | 2021007012 A1 | 1/2021 |
| WO | 2021007234 A1 | 1/2021 |
| WO | 2021174672 A1 | 9/2021 |
| WO | 2021183770 A1 | 9/2021 |

* cited by examiner

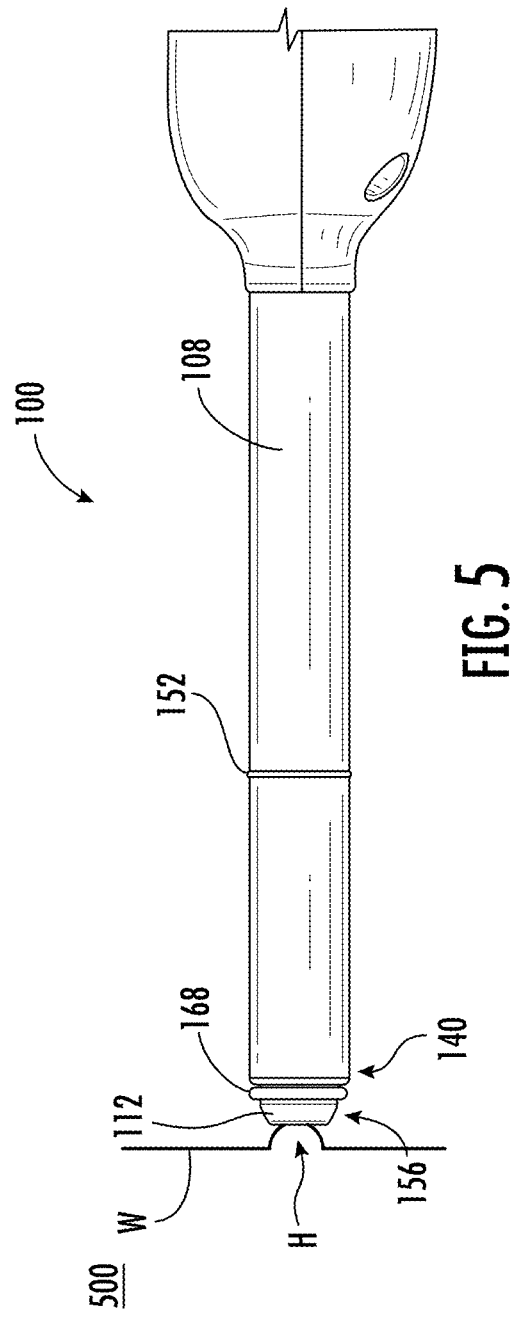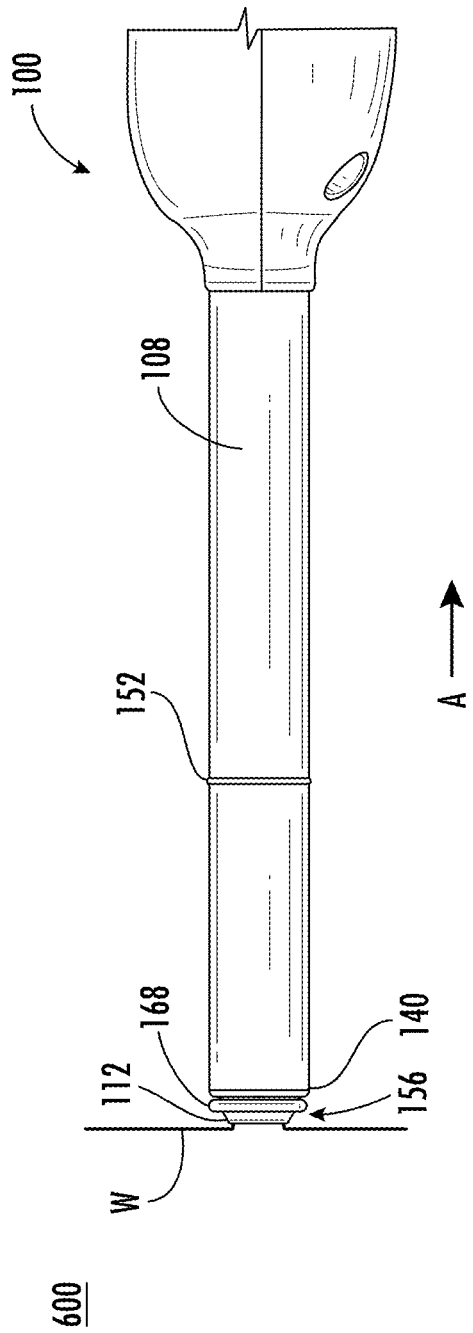

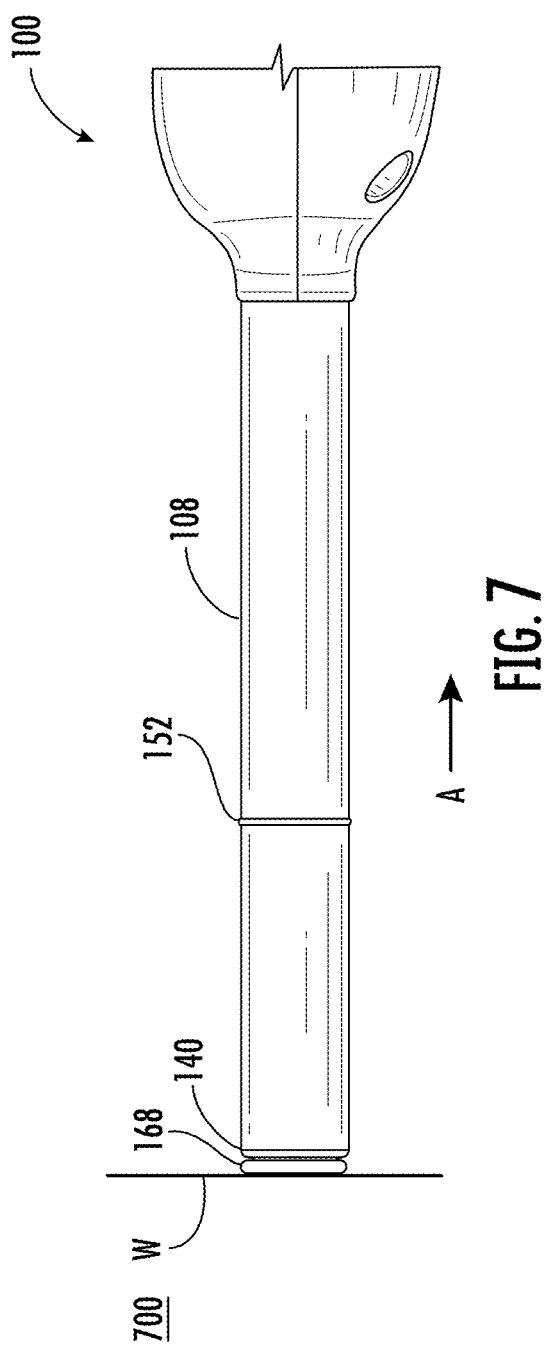
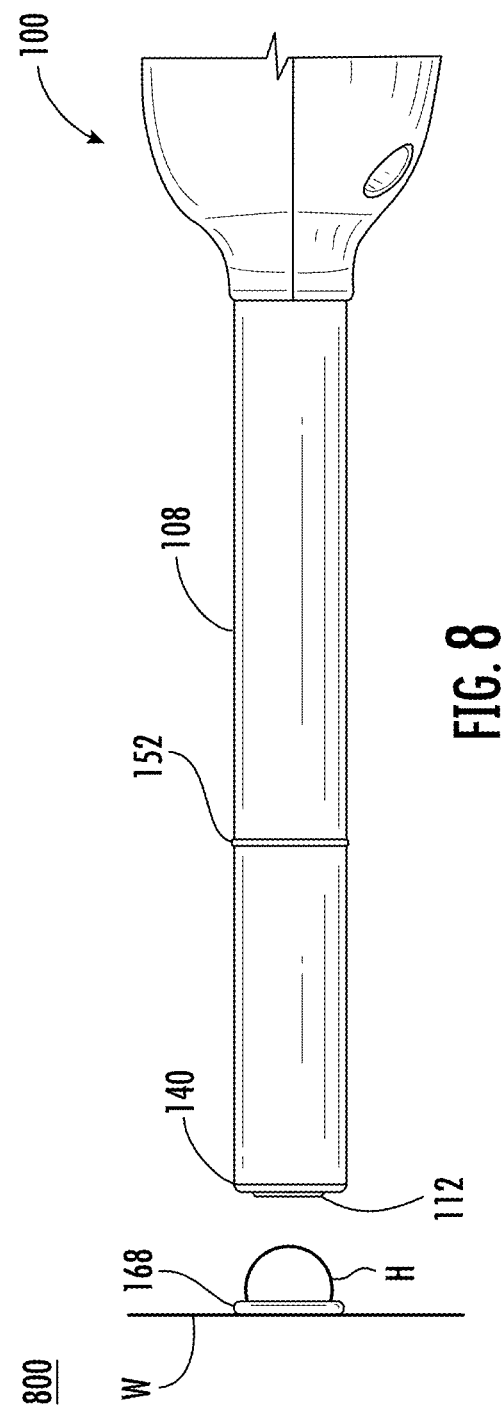

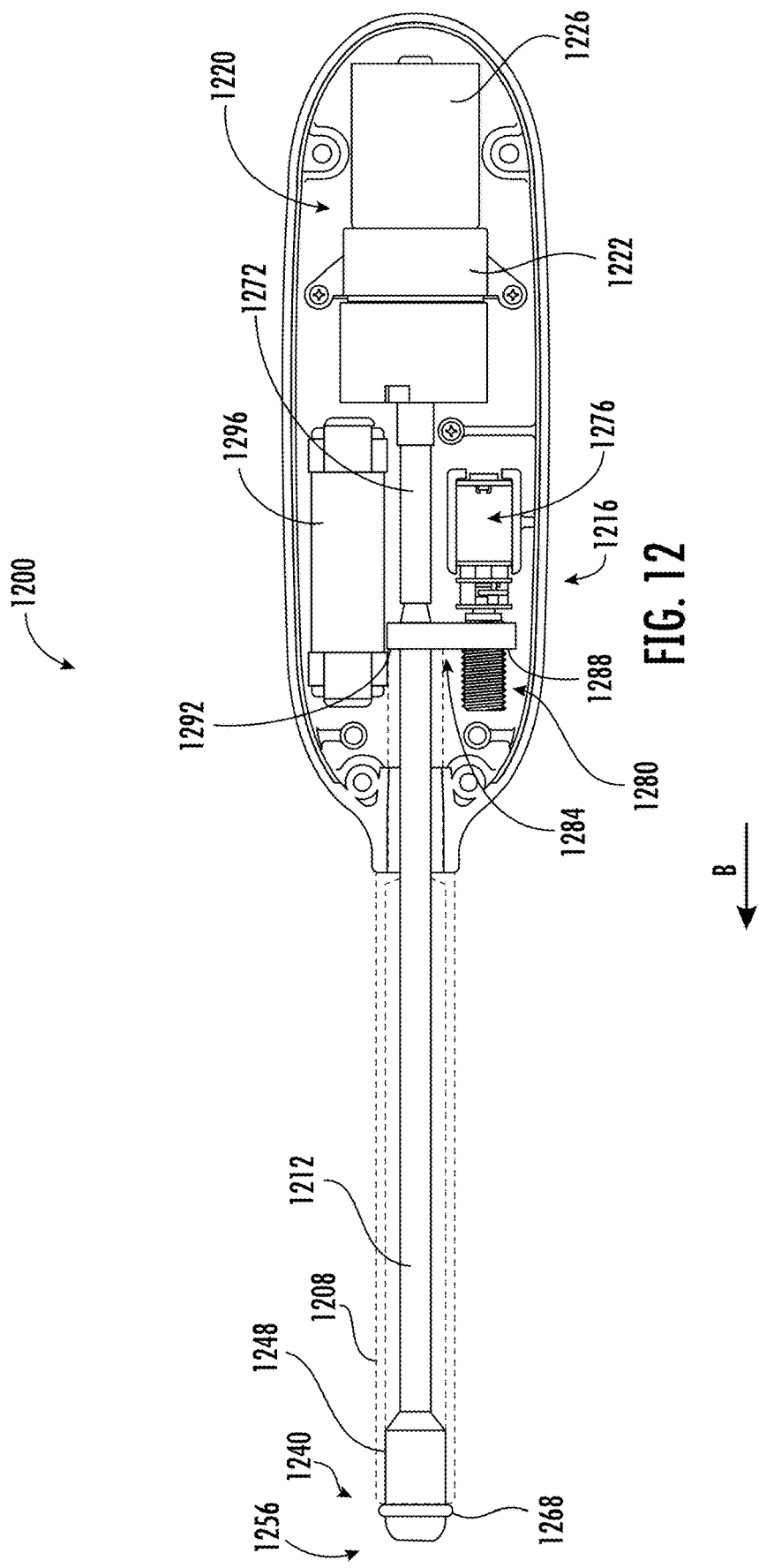

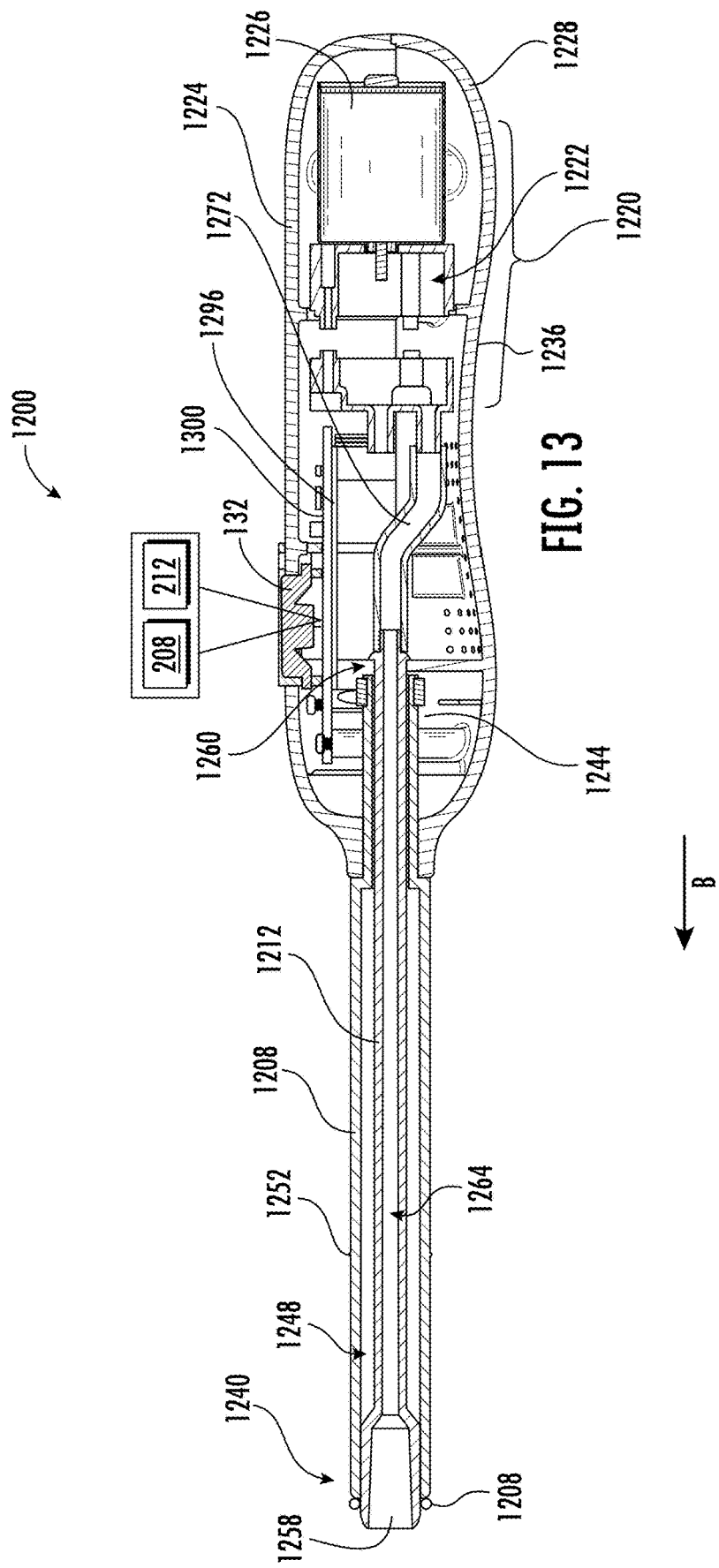

HEMORRHOID BANDER AND METHOD OF USE THEREOF

FIELD OF THE TECHNOLOGY

Aspects of the present disclosure relate to a hemorrhoid bander and method of use thereof.

BACKGROUND

Hemorrhoids are swollen veins that can develop in the anus and/or lower rectum. Hemorrhoids may cause bleeding during bowel movements. Prolapsed hemorrhoids may result in pain and/or irritation in the anus and/or lower rectum.

Hemorrhoids may be treated using rubber band ligation. During a rubber band ligation procedure, a hemorrhoid bander is used to position one or two rubber bands over the base of the hemorrhoid to constrict blood flow to the hemorrhoid. The hemorrhoid then withers and falls off.

SUMMARY

In some aspects of the present disclosure, a hemorrhoid bander includes a housing, an actuation system positioned within the housing, a power source positioned within the housing, an outer shaft defining a hollow passageway, and an inner shaft positioned within the hollow passageway of the outer shaft. The power source is configured to provide power to the actuation system. The inner shaft includes a distal end having an opening, a hollow passageway, and a proximal end. The inner shaft and the outer shaft are relatively movable between a first relative position and a second relative position. The actuation system is coupled to a proximal end of a first one of the inner shaft or the outer shaft and configured to change the inner shaft and the outer shaft between the first relative position and the second relative position, and a second one of the inner shaft and the outer shaft is fixedly coupled to the housing.

In some aspects, a hemorrhoid bander includes a housing, a pump positioned within the housing, an outer shaft coupled to the housing, the outer shaft defining a hollow passageway, and an inner shaft positioned within the hollow passageway of the outer shaft. One of the inner shaft or the outer shaft is relatively movable. The inner shaft includes a distal end having an opening, a hollow passageway, and a proximal end. The proximal end of the inner shaft is coupled to the pump such that the pump is in fluid communication with the hollow passageway and the opening of the inner shaft.

In some aspects, a method of operation of a hemorrhoid bander includes commanding, by a controller, a pump positioned within a housing of the hemorrhoid bander to generate a suction force to pull a hemorrhoid into an opening in an inner shaft of the hemorrhoid bander. The method includes commanding, by the controller, a powered actuation system positioned within the housing of the hemorrhoid bander to retract the inner shaft, such that an outer shaft of the hemorrhoid bander pushes a rubber band off of a distal end of the inner shaft and onto the hemorrhoid as the inner shaft is retracted or commanding, by the controller, the powered actuation system to extend the outer shaft, such that the outer shaft of the hemorrhoid bander pushes the rubber band off of the distal end of the inner shaft and onto the hemorrhoid as the outer shaft is extended.

In some aspects, a controller includes a processor and a memory configured to store instructions. The processor is configured to execute the instructions to responsive to a user input, activate a pump positioned within a housing of a hemorrhoid bander to pull a hemorrhoid into an opening in an inner shaft of the hemorrhoid bander; actuate a powered actuation system within the housing of the hemorrhoid bander to: retract the inner shaft such that an outer shaft of the hemorrhoid bander pushes a rubber band off of a distal end of the inner shaft and onto the hemorrhoid as the inner shaft is retracted; or extend the outer shaft such that the outer shaft of the hemorrhoid bander pushes the rubber band off of the distal end of the inner shaft and onto the hemorrhoid as the outer shaft is extended.

Additional advantages and novel features of these aspects will be set forth in part in the description that follows, and in part will become more apparent to those skilled in the art upon examination of the following and learning by practice of the disclosure.

BRIEF DESCRIPTION OF THE FIGURES

FIG. 5 illustrates a distal end of the hemorrhoid bander of FIG. 1 in a starting position of a hemorrhoid ligation process, in accordance with aspects of the present disclosure.

FIG. 6 illustrates the distal end of the hemorrhoid bander of FIG. 1 in an intermediate position of a hemorrhoid ligation process, in accordance with aspects of the present disclosure.

FIG. 7 illustrates the distal end of the hemorrhoid bander of FIG. 1 in another intermediate position of a hemorrhoid ligation process, in accordance with aspects of the present disclosure.

FIG. 8 illustrates the distal end of the hemorrhoid bander of FIG. 1 in an ending position of a hemorrhoid ligation process, in accordance with aspects of the present disclosure.

FIG. 12 illustrates a top view of another hemorrhoid bander, with a portion of a housing removed and an outer shaft shown as transparent, in accordance with aspects of the present disclosure.

FIG. 13 illustrates a cross-sectional view of the hemorrhoid bander of FIG. 12 in accordance with aspects of the present disclosure.

DETAILED DESCRIPTION

Figure 1:
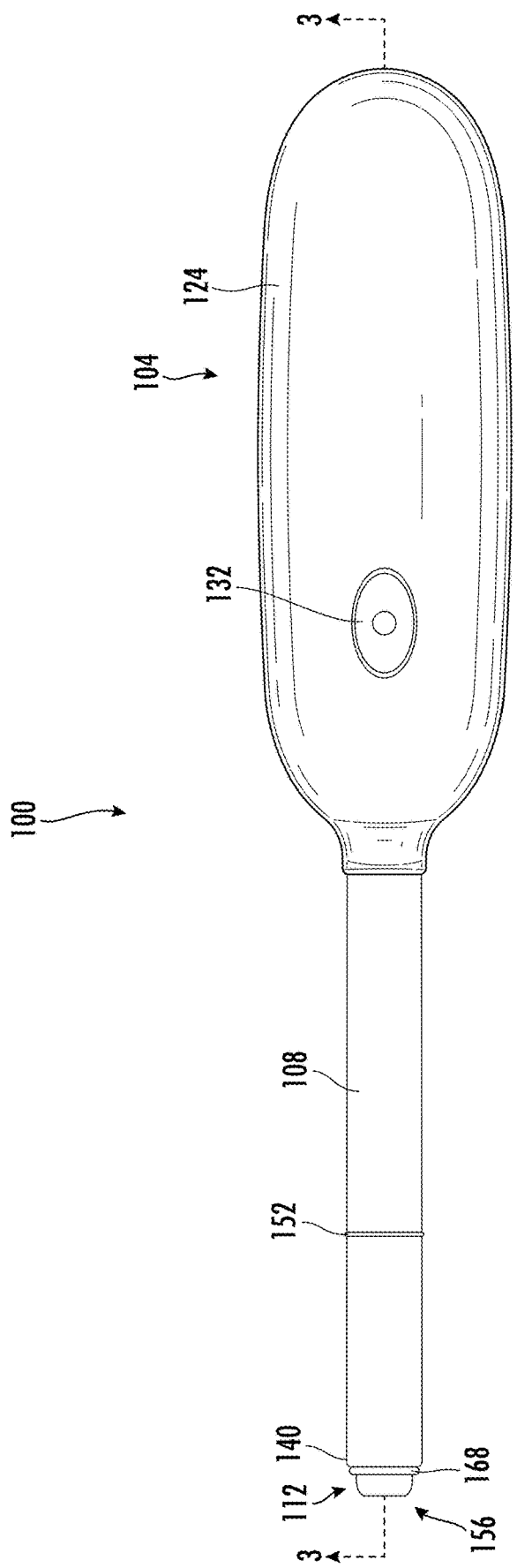
FIG. 1 illustrates a top view of a hemorrhoid bander, in accordance with aspects of the present disclosure.
Figure 2:
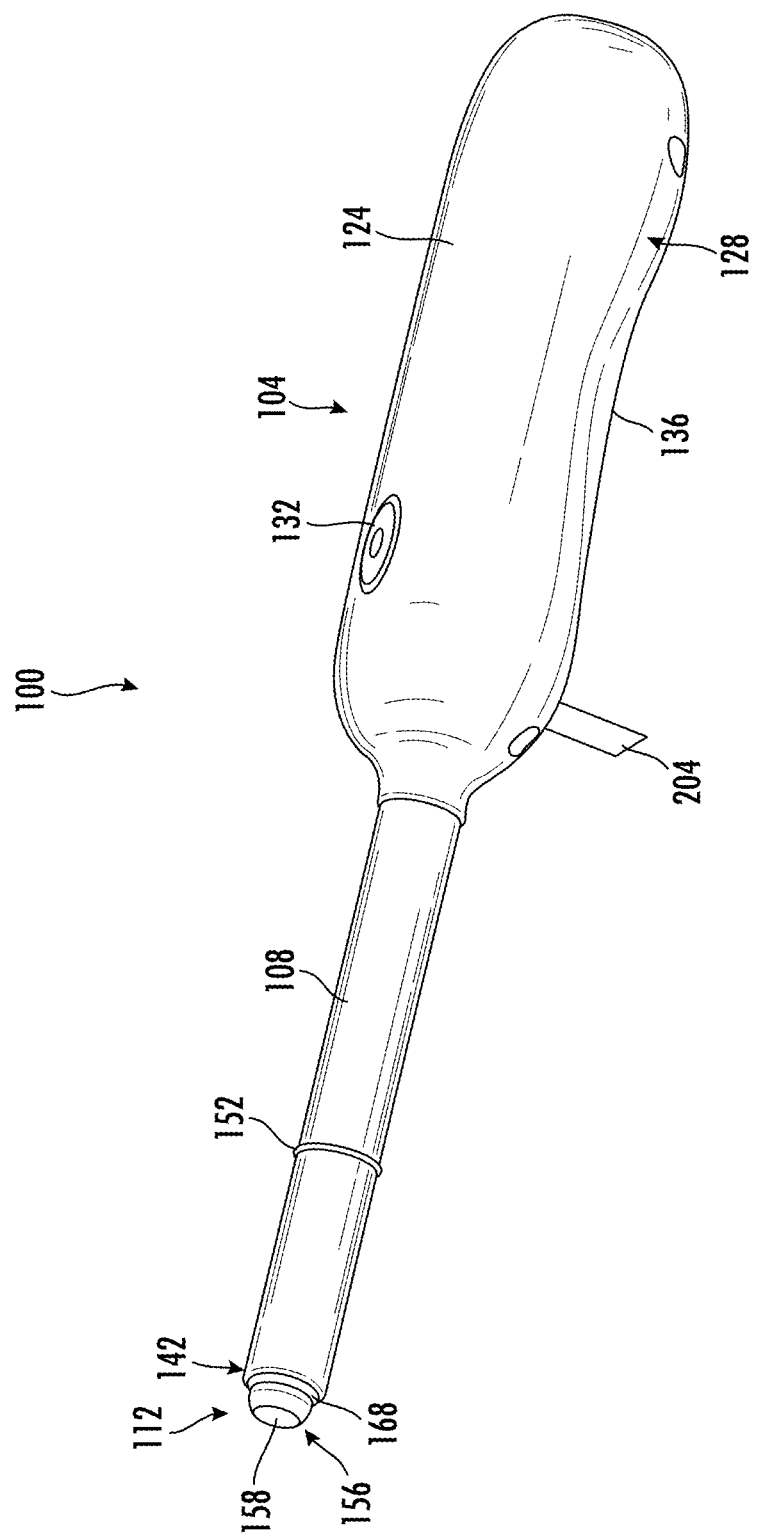
FIG. 2 illustrates a perspective view of the hemorrhoid bander of FIG. 1, in accordance with aspects of the present disclosure.

The disclosure relates to a hemorrhoid bander and method of use thereof. As discussed herein, the hemorrhoid bander has various advantages and novel features compared to prior hemorrhoid banders and methods of using the same.

During a rubber band ligation procedure, suction is typically used to draw a portion of the tissue surrounding the hemorrhoid into a portion of a hemorrhoid bander or ligator. A rubber band is then pushed onto the base of the hemorrhoid.

Conventional hemorrhoid ligators may include a syringe having a plunger that a practitioner can pull to create suction to pull the tissue surrounding the hemorrhoid into a portion of the hemorrhoid ligator. Such hemorrhoid ligators require the use of two hands as it is necessary to hold the hemorrhoid ligator into position with one hand and actuate the plunger with the other hand. Such hemorrhoid ligators also include a manually-actuated slider to push a rubber band coupled to the end of the tip of the hemorrhoid ligator onto the base of the hemorrhoid. Since the practitioner needs to a) hold the hemorrhoid ligator in position, b) actuate the plunger to generate suction, and c) actuate the slider to push the rubber band onto the hemorrhoid, such hemorrhoid ligators require the use of two hands and/or a second person (e.g., practitioner's assistant).

Other types of conventional hemorrhoid ligators may be coupled to an external suction source, such as a wall-mounted suction source, wherein the coupling mechanism includes tubing. In such aspects, the hemorrhoid ligator typically includes a trigger that a practitioner can pull to create the suction that pulls the tissue surrounding the hemorrhoid into a portion of the hemorrhoid ligator. Such hemorrhoid ligators include a manually-actuated slider to push a rubber band coupled to the end of the tip of the hemorrhoid ligator onto the base of the hemorrhoid. Since the practitioner needs to a) hold the hemorrhoid ligator in position, b) actuate the trigger to generate suction, and c) actuate the slider to push the rubber band onto the hemorrhoid, such hemorrhoid ligators are difficult to use with one hand, and often require the use of an assistant. Moreover, the tubing can get in the way of the practitioner, which complicates the procedure.

Unlike external suction source ligators, the hemorrhoid bander described herein is capable of operation without an external suction source such as, for example, a wall-mounted suction source that is not in the housing of hemorrhoid bander.

Additionally, conventional hemorrhoid ligators that require the use of manually-actuated suction sources and/or sliders to push the rubber band onto the hemorrhoid typically move after the hemorrhoid ligator has been inserted. Therefore, conventional hemorrhoid ligators are typically used with an anoscope to allow the practitioner to compensate for movement of the hemorrhoid ligator.

Unlike these prior hemorrhoid ligators, the hemorrhoid bander described herein is capable of operation using a single hand. Indeed, in the hemorrhoid bander described herein, the practitioner uses one hand to position the hemorrhoid bander in the patient's anus, uses the thumb of the hand holding the hemorrhoid bander to actuate a start button, and continues holding the hemorrhoid bander in position until the hemorrhoid bander positions a rubber band around the base of the hemorrhoid. In other aspects, the hemorrhoid bander described herein is not adapted for use with two hands (e.g., the practitioner does not need to hold the hemorrhoid bander in position with one hand while actuating actuators and/or suction mechanisms with their other hand).

Aspects of the present disclosure relate to a hemorrhoid bander configured to allow an automated hemorrhoid ligation procedure. The hemorrhoid bander includes an onboard vacuum pump configured to generate a suction force configured to pull a hemorrhoid and/or tissue into a shaft of the hemorrhoid bander. The hemorrhoid bander also includes an onboard powered actuation system configured to push a rubber band off of the shaft of the hemorrhoid bander and onto the hemorrhoid and/or tissue being held by the suction force. A practitioner can operate the hemorrhoid bander with one hand and hold it steady during the hemorrhoid banding procedure, such that it is not necessary to use an anoscope to verify the position of a distal end of the hemorrhoid bander during the hemorrhoid banding procedure.

Referring to FIGS. 1-4, the hemorrhoid bander 100 includes a housing 104 connected to an outer shaft 108 and an inner shaft 112 that are relatively movable, an actuation system 116 for controlling motion of at least one of the inner shaft 112 or outer shaft 108, and a pump 120 for providing a suction force within the inner shaft 112 to pull a hemorrhoid and/or tissue within the inner shaft 112. The actuation system 116 and the pump 120 are wholly contained within the housing 104. The actuation system 116 and the pump 120 are powered by a power source 196 positioned within the housing 104.

The housing 104 includes a first or upper portion 124 fixedly connected to a second or lower portion 128. The upper portion 124 of the housing 104 includes a start button 132 configured to begin a hemorrhoid banding procedure executable by the hemorrhoid bander 100 as described herein. In some aspects, the lower portion 128 of the housing 104 includes a contoured portion 136 configured to be easily graspable by a practitioner. The contoured portion 136 may be shaped such that the practitioner's thumb overlies the start button 132 when the practitioner is holding the hemorrhoid bander 100 in an operational position. The housing 104 may be made from a plastic, metal, composite, or ceramic material, or any combination thereof.

The outer shaft 108 includes a first or distal end 140 spaced apart from an opposing second or proximal end 144 (FIG. 3), and a hollow passageway 148 (FIG. 3) defined by the inner wall(s) of the outer shaft 108. In one exemplary implementation, but not limited hereto, the proximal end 148 of the outer shaft 108 is coupled to the housing 104 such that the outer shaft 108 is axially fixed relative to the housing 104. The passageway 148 is sized to movably receive the inner shaft 112 therein. For example, an inner dimension between the inner wall(s) of the outer shaft 108 is greater than the outer dimension of the outer wall(s) of the inner shaft 112. In some aspects, the outer shaft 108 includes a marking 152 positioned to indicate that the outer shaft 108 has penetrated sufficiently deeply into an anus of a patient to begin the hemorrhoid banding procedure. In some aspects, an outer diameter of the outer shaft 108 is about 18 millimeters (mm) to about 12 mm. In some aspects, an outer diameter of the outer shaft 108 is less than or equal to about 15 mm.

Although the outer shaft 108 and inner shaft 112 are illustrated as having a circular cross-section, it should be understood that other cross-sectional shapes (e.g., square, rectangle, oval) may be utilized. In one example, the outer shaft 108 is substantially cylindrical. In this example, the diameter of the outer shaft 108 is substantially the same along the length of the outer shaft 108 (e.g., from the distal end 140 to the proximal end 144). For example, the diameter of the outer shaft 108 does not increase towards the proximal end 144 of the outer shaft 108.

The inner shaft 112 includes a first or distal end 156 spaced apart from an opposing second or proximal end 160, and a hollow passageway 164 (FIG. 3) defined by the inner wall of the inner shaft 112. In one exemplary implementation, which should not be construed as limiting, the inner shaft 112 is slidingly movable within and/or relative to the outer shaft 108 and/or the housing 104, such that the inner shaft 112 can be retracted in a direction relative to the outer shaft 108 as indicated by the arrow A. The distal end 156 of the inner shaft 112 includes an opening 158 (FIG. 3) in fluid communication with the hollow passageway 164. The distal end 156 of the inner shaft 112 is smooth and/or rounded, which may facilitate insertion of the hemorrhoid bander 100 into the patient without the use of an anoscope.

Figure 3:
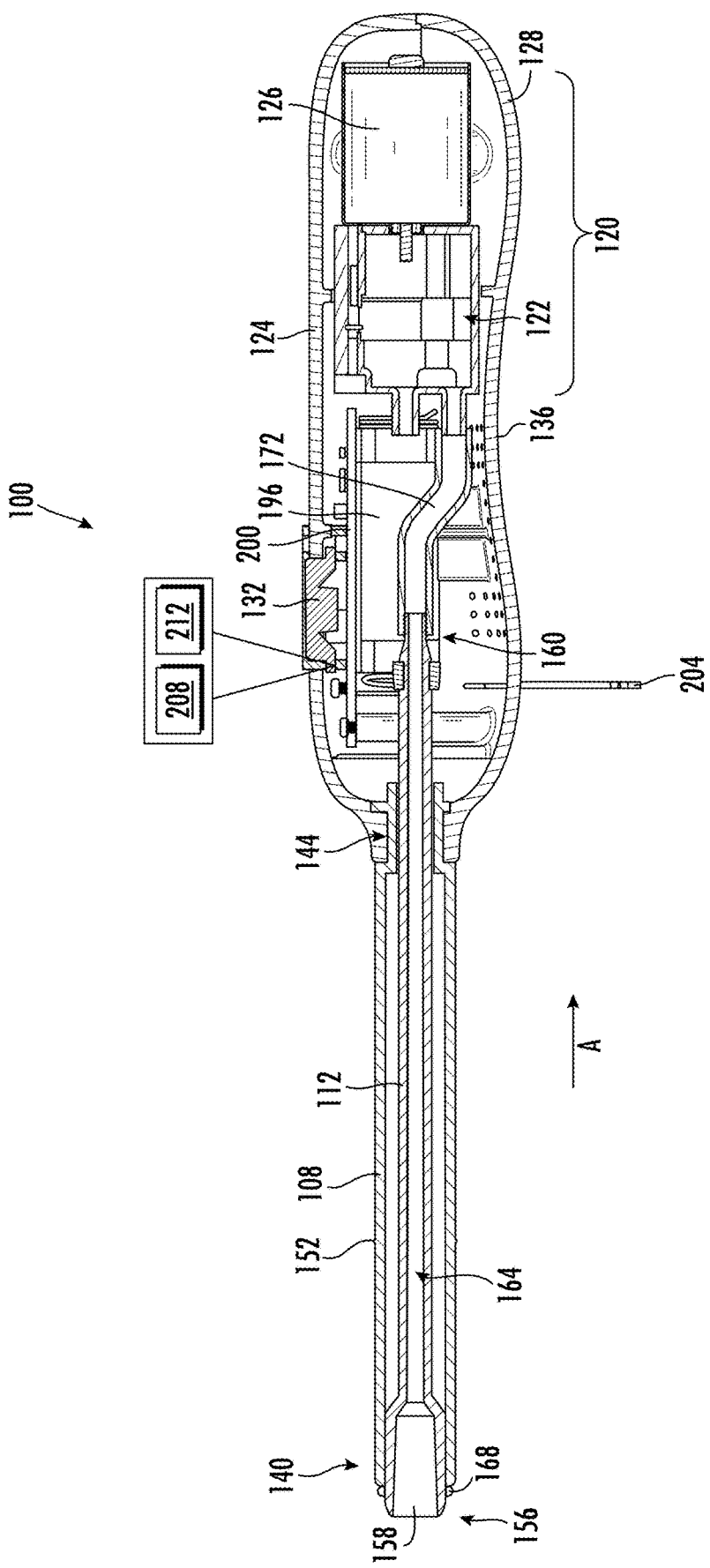
FIG. 3 illustrates a cross-sectional view of the hemorrhoid bander of FIG. 1, taken along line 3-3 of FIG. 1, in accordance with aspects of the present disclosure.
Figure 4:
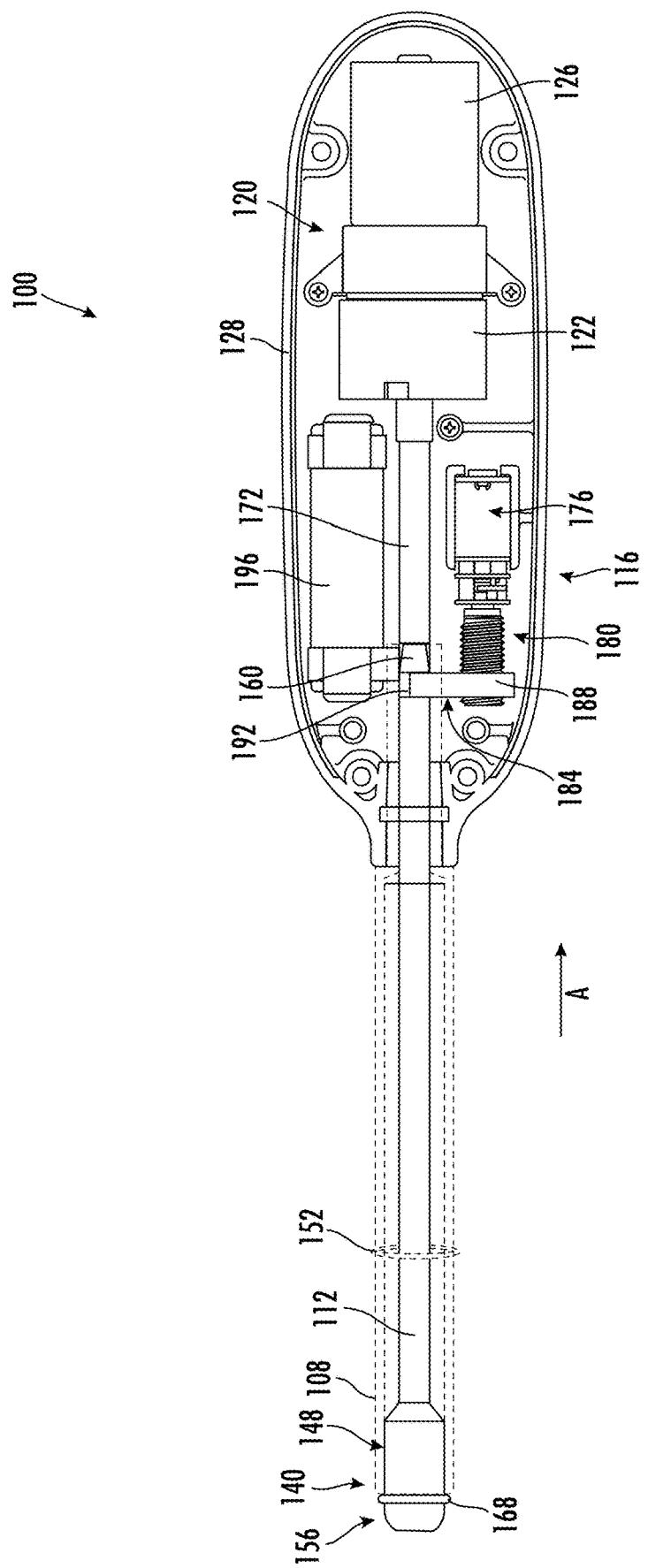
FIG. 4 illustrates a top view of the hemorrhoid bander of FIG. 1 with a portion of a housing removed and an outer shaft shown as transparent, in accordance with aspects of the present disclosure.

Referring to FIG. 5 in addition to FIGS. 3 and 4, the distal end 156 of the inner shaft 112 is configured to receive at least one rubber band 168 and hold the at least rubber band 168 in an expanded state. For example, each rubber band 168 may be formed from an elastomeric and/or rubber material having a non-expanded or resting state, and an expanded state in which the rubber band exerts a compressive force relative to the non-expanded or resting state. In some aspects, the distal end 156 of the inner shaft 112 may be configured to receive one rubber band 168, while in other aspects, the distal end 156 of the inner shaft 112 may receive a plurality of rubber bands 168, such as but not limited to up to four rubber bands 168, where a number of rubber bands 168 may depend on a size of a hemorrhoid, a diameter or width of each rubber band 168, a compressive force of each rubber band 168, and/or an available shaft length on the inner shaft 112 for holding the rubber band(s) 168. In some aspects, the distal end 156 of the inner shaft 112 may include one or more grooves, ridges, or other mounting features configured to receive the rubber band(s) 168 and maintain a position of the rubber band(s) 168 on the inner shaft 112. In some aspects, the hemorrhoid bander 100 may be preloaded with the rubber band(s) 168. In other aspects, the rubber band(s) 168 may be manually loaded onto the distal end 156 of the inner shaft 112.

In some aspects, the distal end 156 of the inner shaft 112 may include an illuminated portion, such as a lighting device, and/or at least some portion of the inner shaft 112 may include a light transmissive material (e.g., clear plastic material, one or more optical fibers) for transferring light from a lighting device (e.g., a light emitting diode) mounted within the housing 104 to the distal end of the inner shaft 112. In some aspects, the inner shaft 112 and the outer shaft 108 may be made of A1 grade plastic.

Referring back to FIGS. 3 and 4, the proximal end 160 of the inner shaft 112 is fluidly coupled to the pump 120 via suction tubing 172. The pump 120 is operable to generate suction through the suction tubing 172 and the hollow passageway 164. In the illustrated aspect, the pump 120 is a vacuum pump that includes a pump motor 126 that operates to remove air and/or liquid from a compression chamber 122 fluidly connected to the suction tubing 172, resulting in at least a partial vacuum within the compression chamber 122 that creates a suction force at the opening 158 of the suction tubing 172, and hence at the distal end 156 of the inner shaft 112 via the hollow passageway 164. Although, it should be understood that the pump 120 may include any other type of mechanism operable to create at least a partial vacuum and hence the suction force at the opening 158 of the suction tubing 172. As described in greater detail below, when the hemorrhoid bander 100 is deployed in a patient, the suction produced by the pump 120 can suck the hemorrhoid, and/or tissue at or proximate the hemorrhoid, into the opening 158 in the distal end 156 of the inner shaft 112. Since the hemorrhoid bander 100 includes the pump 120, it is not necessary to use any manually-actuated suction sources, such as a plunger to generate suction. Further, it is not necessary to couple the hemorrhoid bander 100 to an external suction source, such as a wall-mounted suction source. Thus, the integral pump 120 of the hemorrhoid bander 100 improves an ease of use and efficiency of the hemorrhoid bander 100. The hemorrhoid bander 100 does not rely on any manually-actuated suction sources such as plungers. The hemorrhoid bander 100 does not rely on any externally-powered suction sources, such as wall-mounted suction sources that are not positioned within the housing 104.

As shown in FIG. 4, the actuation system 116 is coupled near the proximal end 160 of the inner shaft 112 and is configured to actuate the inner shaft 112 in the direction indicated by the arrow A. In the illustrated aspect, the actuation system 116 includes a motor 176 operable to move a drive train 180, which in turn is operable to move a coupling 184 to effect movement of the inner shaft 112. In the illustrated aspect, the output of the motor 176 a rotary output and is coupled to the drive train 180 and configured to rotate the drive train 180. In the illustrated aspect, the drive train 180 includes a threaded shaft. In other aspects, the drive train 180 may include one or more gears. In other aspects, the motor 176 may have a linear output and may be configured to push drive train components 180 and/or the inner shaft 112 in the direction indicated by the arrow A. In other aspects, the actuation system 116 may include a magnetic drive system and/or a piston system instead of the motor 176. The inner shaft 112 is not pushed by thumb or fingers of the practitioner to move the inner shaft 112 in the direction indicated by the arrow A.

The coupling 184 includes a first portion 188 fixedly coupled to the inner shaft 112 proximate the proximal end 160 of the inner shaft 112 and a second portion 192 movably coupled to the drive train 180. For example, in the illustrated aspect, the second portion 192 may be threadably coupled to the threaded shaft 180. Although, alternatively, the second portion 192 of the coupling may include any surface that can interact with threaded shaft 180, and/or a gear mechanism in the case where the drive train 180 includes one or more gears. Also, alternatively, the second portion 192 may be a fixed connection mechanism in a case where the drive train 180 is a linear drive system, a magnetic drive system, and/or a piston drive system.

Referring to FIGS. 5-8, in the illustrated example, rotation of the threaded shaft 180 by the motor 176 can cause the coupling 184 to travel along the direction indicated by the arrow A, thereby retracting the inner shaft 112 in the direction indicated by the arrow A, and moving the inner shaft 112 from a starting position to an ending position of the hemorrhoid ligation process described herein. As the inner shaft 112 retracts and/or moves relative to the outer shaft 108, the distal end 140 of the outer shaft 108 pushes the rubber band(s) 168 towards the distal end 156 of the inner shaft 112, as shown in FIGS. 6 and 7. As the inner shaft 112 continues to retract, the distal end 140 of the outer shaft 108 pushes the rubber band 168 off of the distal end 156 of the inner shaft 112 and around the hemorrhoid and/or the tissue surrounding the hemorrhoid, as shown in FIG. 8, wherein the rubber band(s) 168 can then exert a compressive force on the hemorrhoid and/or the tissue surrounding the hemorrhoid in an attempt to return to the non-expanded state. The inner shaft 112 is not pushed by thumb or fingers of the practitioner to move the inner shaft 112 in the direction indicated by the arrow A to push the rubber band 168 off of the distal end 156 of the inner shaft 156 and onto the hemorrhoid H.

FIGS. 12 and 13 illustrate a hemorrhoid bander 1200 according to another aspect to the present disclosure. The hemorrhoid bander 1200 is substantially the same as the hemorrhoid bander 100 and is only discussed in detail herein to the extent that it differs from the hemorrhoid bander 100. Like numbers are used to indicate like parts between the hemorrhoid bander 1200 and the hemorrhoid bander 100. In the aspect illustrated in FIGS. 12-13, rather than the inner shaft 1212 moving relative to the outer shaft 1208, the inner shaft 1212 is axially fixed relative to the housing 1204 and the outer shaft 1208 may be movable by the actuation system 1216. In such aspects, the outer shaft 1208 is movably attached to the housing 1204 and the inner shaft 1212 is fixedly attached to the housing 1204. In such aspects, the proximal end 1244 of the outer shaft 1208 may be coupled to actuation system 1216, for example by the coupling 1284 in a similar manner as described above with respect to the connection to the inner shaft 112 of the hemorrhoid bander 100. In such aspects, rotation of the motor 1276 causes the coupling 1284 to travel in a direction opposite the direction indicated by the arrow B, causing the outer shaft 1208 to extend in the direction indicated by the arrow B (which is the opposite of the direction indicated by the arrow A), pushing the rubber band 1268 off of the distal end 1240 of the outer shaft 1208 and onto the hemorrhoid. The outer shaft 1208 is not pushed by thumb or fingers of the practitioner to move the outer shaft 1208 in the direction indicated by the arrow B to push the rubber band 1268 off of the distal end 1240 of the outer shaft 1208 and onto the hemorrhoid.

Returning to FIGS. 3 and 4, the hemorrhoid bander 100 further includes a power source 196, such as a fixed or removable battery, and a controller 200 configured to control operation of the hemorrhoid bander 100 in the hemorrhoid ligation process described herein. The power source 196 is configured to provide power to the pump 120, the motor 176, and the controller 200. The actuation system 116, the pump 120, the controller 200, and the power source 196 are fully contained within the housing 104.

In some aspects, a pull tab 204 is coupled to the power source 196 to prevent the power source 196 from providing power to the pump 120, the motor 176, and the controller 200. For instance, the pull tab 204 may be a sheet of a non-electrically conductive material (e.g., a plastic material) configured to provide a break in a circuit between the power source 196 and the pump 120, the motor 176, and the controller 200. In such aspects, the pull tab 204 can be removed to allow the power source 196 to connect the circuit and provide power to the pump 120, the motor 176, and the controller 200. In such aspects, the start button 132 may be illuminated in a first color and/or flash after the pull tab has been removed, indicating that the hemorrhoid bander 100 is ready for use.

Returning to FIGS. 5-8, illustrate the various stages of the hemorrhoid ligation process executable by the hemorrhoid bander 100 will now be described in more detail. In FIGS. 5-8, a schematic representation of the inner wall W of a patient's rectum and/or anus that has a hemorrhoid H. FIG. 5 illustrates the hemorrhoid bander 100 at a starting position 500 in which the rubber band 168 positioned on the distal end 156 of the inner shaft 112, adjacent the distal end 140 of the outer shaft 108. In other aspects, the rubber band 168 may be spaced from the outer shaft 108. FIG. 6 illustrates the hemorrhoid bander 100 in an intermediate position 600 in which the inner shaft 112 is partially retracted in the direction indicated by the arrow A. FIG. 7 illustrates another intermediate position 700 in which the inner shaft 112 has been retracted further in the direction indicated by the arrow A, and retraction of the inner shaft 112 is causing the distal end 140 of the outer shaft 108 to push the rubber band off of the inner shaft 112. FIG. 8 illustrates the hemorrhoid bander 100 at the end position 800 of the hemorrhoid ligation process, in which the inner shaft 112 is retracted into the outer shaft 108 and the rubber band 168 has been pushed off of the hemorrhoid bander 100, wherein the rubber band(s) 168 are free to contract around the hemorrhoid H and/or the tissue surrounding the hemorrhoid.

Referring back to FIG. 3, the controller 200 includes a memory 208 and a processor 212 configured to carry out computer-executable instructions stored in the memory 208 to control execution of the hemorrhoid ligation process by the hemorrhoid bander 100 as described herein. The controller 200 is configured to actuate components of the hemorrhoid bander 100 to carry out a hemorrhoid banding procedure. The start button 132 is communicatively coupled to the controller 200 such that depressing of the start button 132 may initiate an hemorrhoid ligation process. For example, in one implementation that should not be construed as limiting, after the start button 132 has been depressed, the controller 200 may illuminate the start button 132 in a second color different from the first color and/or stop flashing, indicating that the hemorrhoid banding procedure is in progress. In response to depression of the start button 132, and with the distal end of the hemorrhoid bander 100 positioned adjacent to the hemorrhoid of interest, the controller 200 is configured to activate the pump 120, causing the hemorrhoid and/or the tissue surrounding the hemorrhoid to be sucked into the opening 158 in the distal end 156 of the inner shaft 112. In the illustrated aspect, the controller 200 actuates the motor 176 to retract the inner shaft 112 in the direction indicated by the arrow A (FIGS. 6 and 7). As the inner shaft 112 is retracted, the distal end 140 of the outer shaft 108 contacts the rubber band 168 and pushes the rubber band 168 onto the tissue surrounding the hemorrhoid and/or the hemorrhoid (FIG. 8), where the rubber band 168 is free to contract around the hemorrhoid, resulting in a banded hemorrhoid wherein the rubber band 168 reduces or eliminates a flow of blood to the hemorrhoid. In some aspects, the controller 200 may be configured to actuate the motor 176 to retract the inner shaft 112 a predefined distance to allow the rubber band 168 to be pushed off of the distal end 156 of the inner shaft 112. In such aspects, the controller 200 may be configured to turn off the motor 176 after the inner shaft 112 has been retracted by the predefined distance. In some aspects, the controller 200 may be configured to turn off the pump 120 after the inner shaft 112 has been retracted by the predefined distance, releasing the banded hemorrhoid and/or the tissue surrounding the banded hemorrhoid from the hemorrhoid bander 100. After the pump 116 and the motor 176 have been turned off, the controller 200 may illuminate the start button 132 in the first color and/or flash, indicating that the hemorrhoid banding procedure is complete.

In some aspects, the controller 200 may be configured to actuate the motor 176 to retract the inner shaft 112 for a predefined time period to allow the rubber band 168 to be pushed off of the distal end 156 of the inner shaft 112. In such aspects, the controller 200 may be configured to turn off the motor 176 after the predefined time period. In some aspects, the controller 200 may be configured to turn off the pump 120 after the predefined time period, releasing the banded hemorrhoid and/or the tissue surrounding the banded hemorrhoid from the hemorrhoid bander 100.

In some aspects, the controller 200 may actuate the hemorrhoid ligation process without further intervention from the practitioner once the hemorrhoid bander 100 has been positioned in the patient and the start button 132 has been depressed.

In some aspects, controller 200 may be configured to pause or stop the execution of the hemorrhoid ligation process by the hemorrhoid bander 100 in response to depression of the start button 132 during the hemorrhoid ligation process. For example, stopping the process may include turning off power to all components so that the hemorrhoid bander 100 may be removed from engagement with the hemorrhoid and/or surround tissue. Alternatively, in some aspects, controller 200 may be configured to execute the hemorrhoid ligation process only in response to a constant depression of the start button 132, e.g., wherein the process is paused or stopped in response to removal of the constant depression of the start button 132.

In some aspects, the controller 200 may be configured to stop operation of the pump 120 and the motor 176 after a predefined time period has elapsed. The predefined time period may be several minutes longer than the amount of time it takes to perform a typical hemorrhoid banding procedure. In such aspects, after the predefined time period has elapsed, the controller 200 may be configured to prevent the pump 120 and the motor 176 from being turned on again.

In aspects in which the hemorrhoid bander 100 includes more than one rubber band 168, the controller 200 may be configured to actuate the motor 176 to retract the inner shaft 112 a first predefined distance to allow the first rubber band 168 to be pushed off of the distal end 156 of the inner shaft 112 while the other rubber bands 168 remain on the distal end 156 of the inner shaft 112. For a subsequent ligation, the controller 200 may be configured to actuate the motor 176 to retract the inner shaft 112 a second predefined distance to allow the second rubber band 168 to be pushed off of the distal end 145 of the inner shaft 112 while the other rubber bands 168 remain on the distal end 156 of the inner shaft 112, and so forth.

In aspects in which the inner shaft 112 may be axially fixed relative to the housing 104 and the outer shaft 108 is movable relative to the housing 104 and the inner shaft 112, the controller 200 is configured to actuate the motor 176 to extend the outer shaft 108 in a direction opposite the direction indicated by the arrow A, as describe above. In such aspects, extension of the outer shaft 108 pushes the rubber band 168 off of the inner shaft 112.

Figure 9:
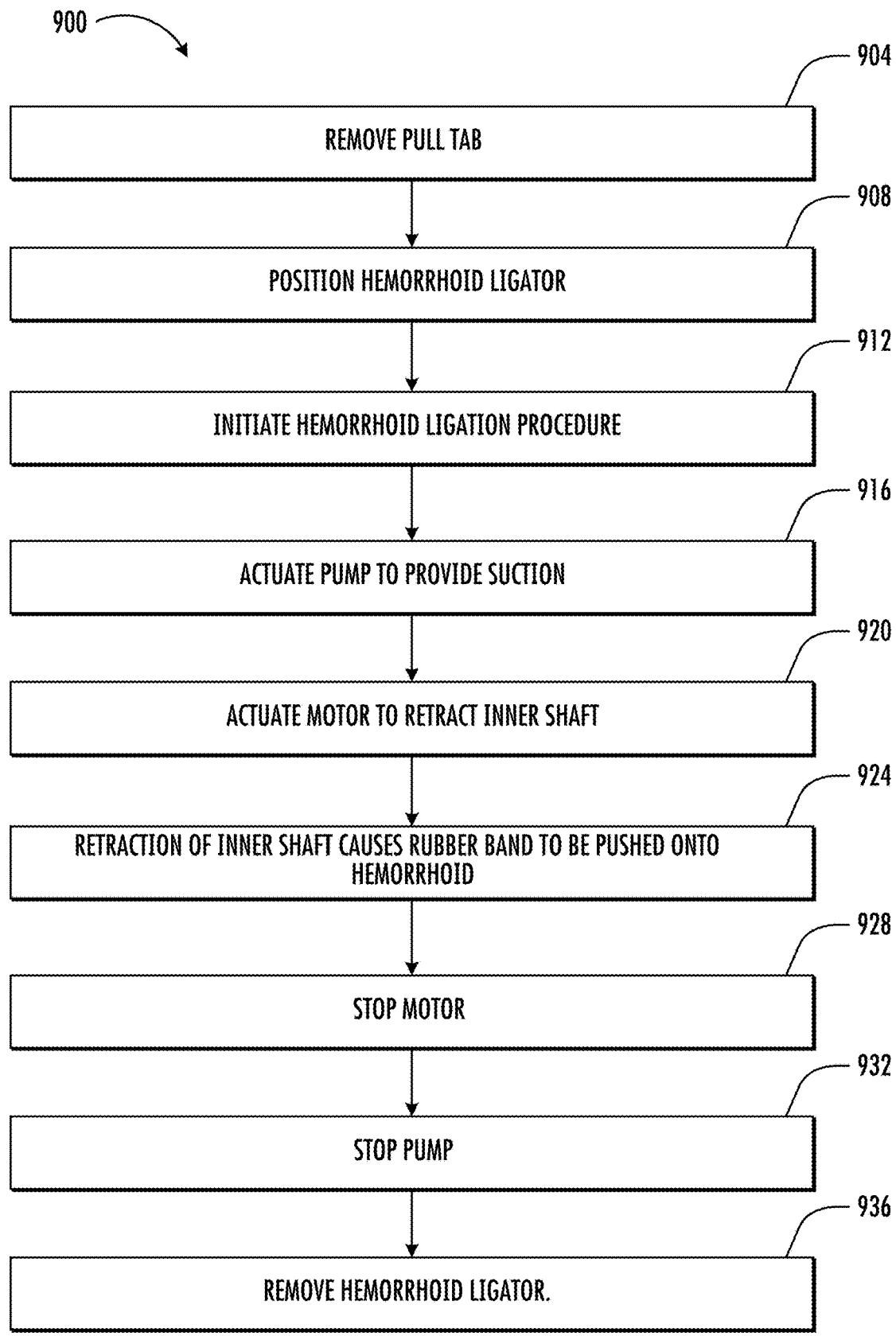
FIG. 9 illustrates a method for using the hemorrhoid bander of FIG. 1 to band a hemorrhoid and/or the tissue near a hemorrhoid, in accordance with aspects of the present disclosure.

FIG. 9 illustrates a method 900 for using the hemorrhoid bander 100 to band a hemorrhoid and/or the tissue near a hemorrhoid. At 904, a practitioner removes the pull tab 204, which causes the power source 196 to provide power to the components of the hemorrhoid bander 100. Once the pull tab 204 has been removed, the start button 132 may be illuminated with a first color and/or flash. At 908, the practitioner positions the hemorrhoid bander 100 in the anus of the patient with one hand. The practitioner may confirm that the marking 152 is no longer visible, and/or that the marking is a predetermined distance relative to an insertion point in the anus of the patient. Positioning the hemorrhoid bander 100 does not require the use of equipment such as an anoscope. At 912, the hemorrhoid ligator 100 receives an input indicating that the hemorrhoid ligation process should be initiated. For example, the practitioner may depress the start button 132 to initiate the hemorrhoid ligation procedure.

After the start button 132 has been depressed, the color of the start button 132 may change to indicate that the hemorrhoid banding process is in progress. In aspects in which the start button 132 began flashing at 902, the start button 132 remains illuminated but stops flashing. At 916, the controller 200 actuates the pump 120 to provide suction via the suction tubing and the inner shaft 112. The hemorrhoid and/or tissue surrounding the hemorrhoid is sucked into the opening 158 in the distal end 156 of the inner shaft 112. At 920, the controller 200 actuates the motor 176 to retract the inner shaft 112. In some aspects, 916 and 920 may occur simultaneously. At 924, retraction of the inner shaft 112 causes the distal end 140 of the outer shaft 108 to push the rubber band 168 onto the hemorrhoid and/or the tissue surrounding the hemorrhoid. At 928, the controller 200 stops the motor 176. In some aspects, the controller 200 stops the motor 176 after the inner shaft 112 has been retracted a predefined distance. At 932, the controller 200 stops the pump 120. At 932, the banded hemorrhoid and/or tissue surrounding the hemorrhoid is released from the inner shaft 112. In some aspects, 928 and 932 may occur simultaneously. At 928 and/or 932, the color of the start button 132 may return to the first color and/or start flashing, indicating that the hemorrhoid banding procedure has been completed. At 936, the practitioner removes the hemorrhoid bander 100 from the patient. It should be understood that 904-908 and 936 are steps that are included to provide context and are not required for the controller 200 to operate the hemorrhoid ligator 100.

In aspects in which the inner shaft 1212 may be axially fixed relative to the housing 1204 and the outer shaft 1208 is movable relative to the housing 1204 and the inner shaft 1212, at 920, the controller 1300 is configured to actuate the motor 1276 to extend the outer shaft 1208 in the direction indicated by the arrow B. In such aspects, extension of the outer shaft 1208 pushes the rubber band 1268 off of the inner shaft 1212. At 928, the controller 1300 may stop the motor 1276 after the outer shaft 1208 has been extended a predefined distance.

In aspects in which the hemorrhoid bander 100 includes multiple rubber bands 168, after 932, the practioner may reposition the hemorrhoid bander 100 and then perform step 908.

After the practitioner has depressed the start button 132 at 908, in some aspects, steps 912-932 are carried out by the controller 200 without further intervention from the practitioner.

The method 900 does not require the practitioner or an assistant to manually actuate any suction devices, such as, for example, a plunger as is used in some conventional hemorrhoid banders. The hemorrhoid bander 100 also is not plugged into an external suction source, such as a wall-mounted suction source. Further, the method 900 does not require the practitioner or an assistant to manually acutate any actuators to push the rubber band 168 off of the inner shaft 112. In contrast, conventional hemorrhoid banders rely on manual actuators to push the rubber band off of the hemorrhoid bander. Therefore, the hemorrhoid bander 100 greatly simplifies hemorrhoid banding procedures, and enables such procedures to be conducted by one practitioner using one hand. This may result in more accurate and easier positioning of the rubber band, since the practitioner does not need to actuate a manual suction source such as a plunger, manually acuate an actuator to push the rubber band off of the ligator, and so forth.

Figure 10:
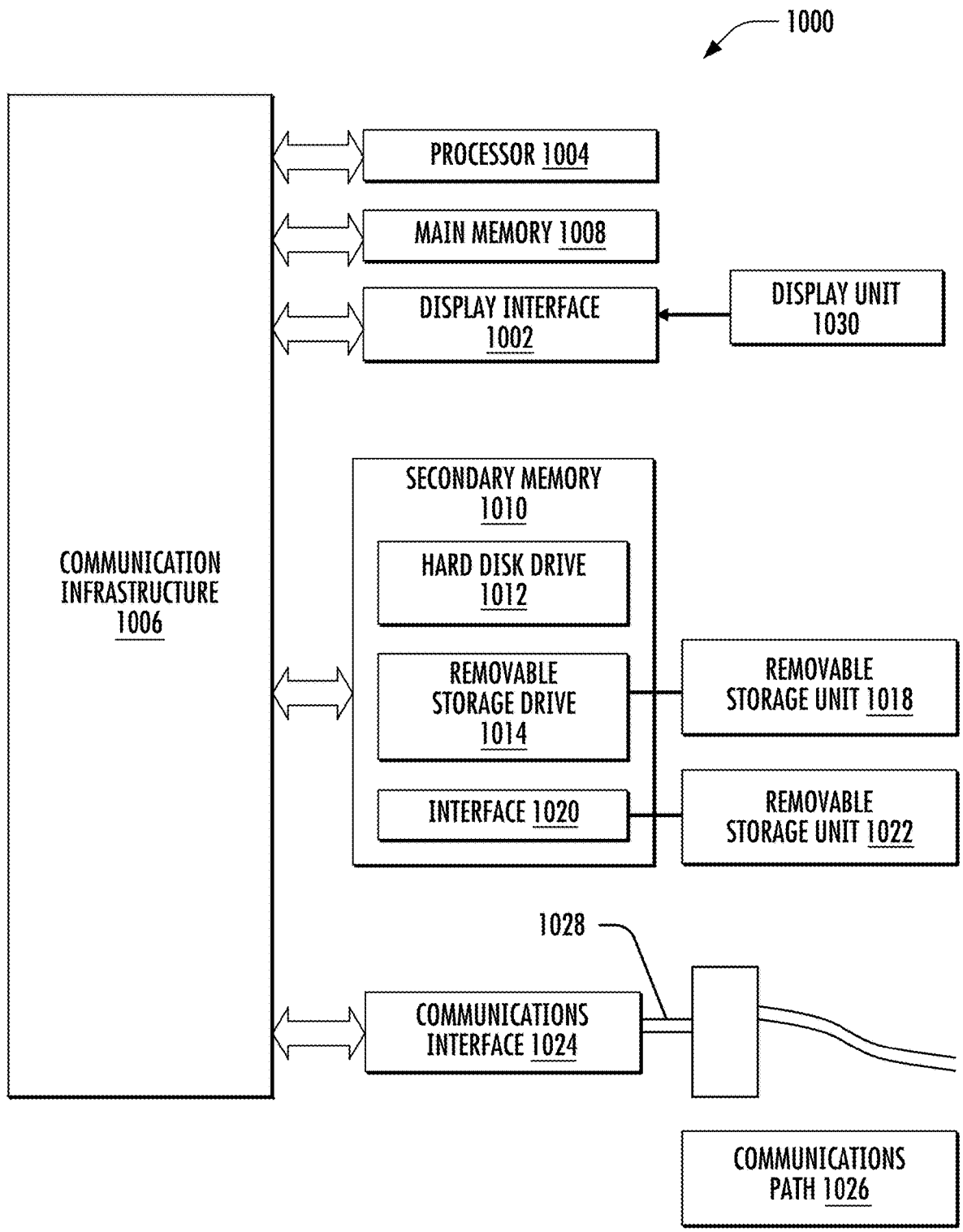
FIG. 10 shows an example system diagram of various hardware components and other features for use with the hemorrhoid bander of FIG. 1 in accordance with aspects of the present disclosure.

FIG. 10 presents an example system diagram of various hardware components and other features, for use in accordance with an aspect of the present disclosure. Aspects of the present disclosure may be implemented using hardware, software, or a combination thereof and may be implemented in one or more computer systems or other processing systems. In one example variation, aspects described herein may be directed toward one or more computer systems capable of carrying out the functionality described herein of the hemorrhoid bander 100. An example of such a computer system 1000 is shown in FIG. 10.

The computer system 1000 includes one or more processors, such as processor 1004. The processor 1004 is connected to a communication infrastructure 1006 (e.g., a communications bus, cross-over bar, or network). The processor 1004 may include a processor for the local computing system 200 of FIG. 3. Various software embodiments are described in terms of this example computer system. After reading this description, it will become apparent to a person skilled in the relevant art(s) how to implement embodiments described herein using other computer systems and/or architectures.

Computer system 1000 may include a display interface 1002 that forwards graphics, text, and other data from the communication infrastructure 1006 (or from a frame buffer not shown) for display on a display unit 1030. Computer system 1000 also includes a main memory 1008, preferably random access memory (RAM), and may also include a secondary memory 1010. The secondary memory 1010 may include, for example, a hard disk drive 1012 and/or a removable storage drive 1014, representing a floppy disk drive, a magnetic tape drive, an optical disk drive, etc. The removable storage drive 1014 reads from and/or writes to a removable storage unit 5018 in a well-known manner. Removable storage unit 1018, represents a floppy disk, magnetic tape, optical disk, etc., which is read by and written to removable storage drive 1014. As will be appreciated, the removable storage unit 1018 includes a computer usable storage medium having stored therein computer software and/or data.

In alternative embodiments, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as that found in video game devices), a removable memory chip (such as an erasable programmable read only memory (EPROM), or programmable read only memory (PROM)) and associated socket, and other removable storage units 1022 and interfaces 1020, which allow software and data to be transferred from the removable storage unit 1022 to computer system 1000. In an example, memory for the computing system 200 may include the main memory 1008, the secondary memory 1010, the removable storage drive 1014, the removable storage unit 1018, the removable storage unit 1022, etc.

The computer system 1000 may also include a communications interface 1024. Communications interface 1024 allows software and data to be transferred between computer system 1000 and external devices. Examples of communications interface 5024 may include a modem, a network interface (such as an Ethernet card), a communications port, a Personal Computer Memory Card International Association (PCMCIA) slot and card, etc. Software and data transferred via communications interface 1024 are in the form of signals 1028, which may be electronic, electromagnetic, optical or other signals capable of being received by communications interface 1024. These signals 1028 are provided to communications interface 1024 via a communications path (e.g., channel) 1026. This path 1026 carries signals 1028 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive, a hard disk installed in a hard disk drive, and/or signals 1028. These computer program products provide software to the computer system 1000. Embodiments described herein may be directed to such computer program products.

Computer programs (also referred to as computer control logic) are stored in main memory 1008 and/or secondary memory 1010. Computer programs may also be received via communications interface 1024. Such computer programs, when executed, enable the computer system 1000 to perform various features in accordance with embodiments described herein. In particular, the computer programs, when executed, enable the processor 1004 to perform such features. Accordingly, such computer programs represent controllers of the computer system 1000.

In variations where embodiments described herein are implemented using software, the software may be stored in a computer program product and loaded into computer system 1000 using removable storage drive 1014, hard disk drive 1012, or communications interface 1020. The control logic (software), when executed by the processor 1004, causes the processor 1004 to perform the functions in accordance with embodiments described herein as described herein. In another variation, embodiments are implemented primarily in hardware using, for example, hardware components, such as application specific integrated circuits (ASICs). Implementation of the hardware state machine so as to perform the functions described herein will be apparent to persons skilled in the relevant art(s).

In yet another example variation, embodiments described herein are implemented using a combination of both hardware and software.

Figure 11:
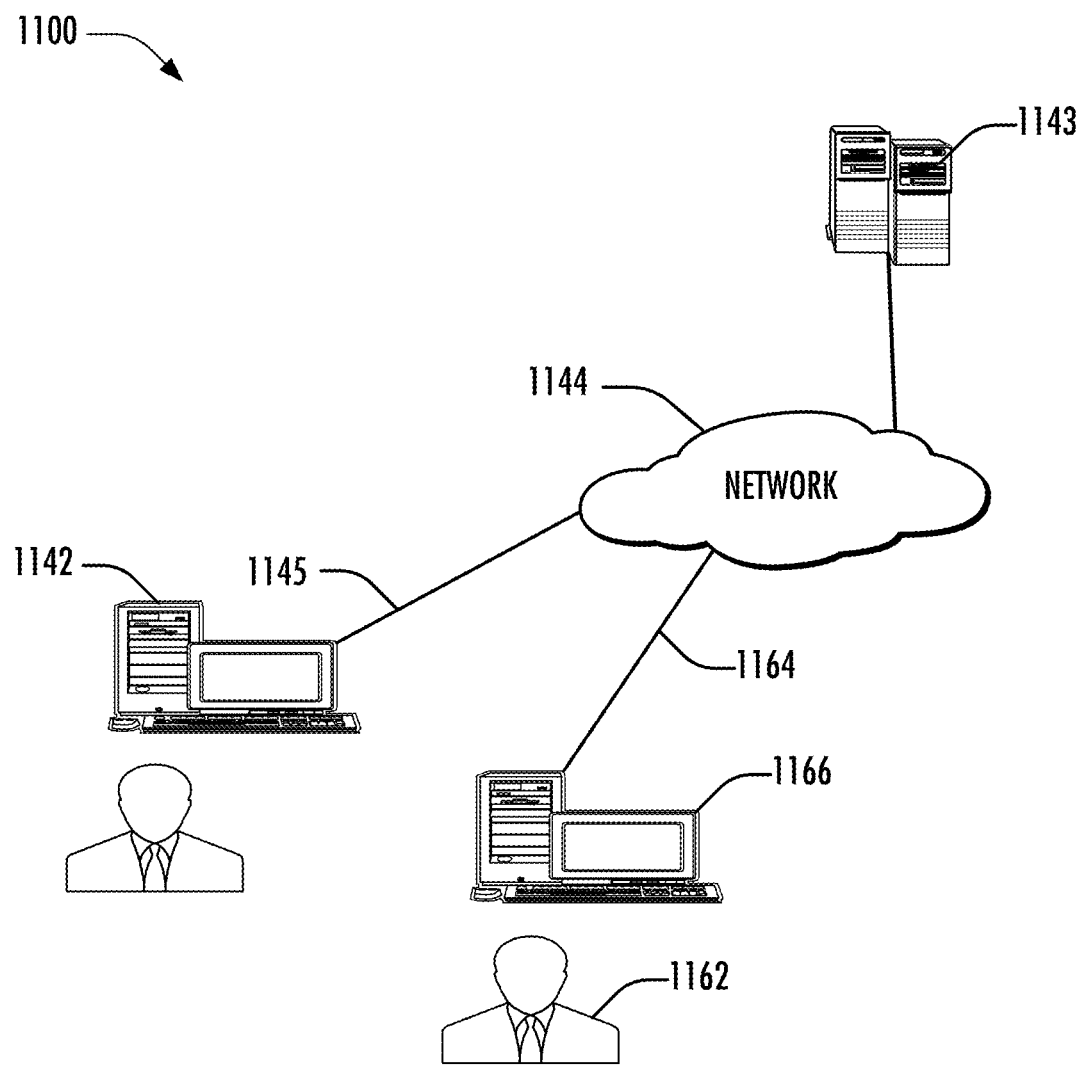
FIG. 11 shows a representative block diagram of various example system components for use with the hemorrhoid bander of FIG. 1 in accordance with aspects of the present disclosure.

FIG. 11 is a block diagram of various example system components for use in accordance with embodiments of the present disclosure. FIG. 11 shows a communication system 1100 usable in accordance with embodiments described herein. The communication system 1100 may include one or more users 1160, 1162 and one or more terminals 1142, 1166. For example, terminals 1142, 1166 may include the control system 1120 or a related system, and/or the like. In one embodiment, data for use in accordance with embodiments described herein is, for example, input and/or accessed by users 1160, 1162 via terminals 1142, 1166, such as personal computers (PCs), minicomputers, mainframe computers, microcomputers, telephonic devices, or wireless devices, such as personal digital assistants ("PDAs") or a hand-held wireless devices coupled to a server 1143, such as a PC, minicomputer, mainframe computer, microcomputer, or other device having a processor and a repository for data and/or connection to a repository for data, via, for example, a network 1144, such as the Internet or an intranet, and couplings 1145, 1146, 1164. The couplings 1145, 1146, 1164 include, for example, wired, wireless, or fiberoptic links. In another example variation, the method and system in accordance with embodiments described herein operate in a stand-alone environment, such as on a single terminal.

Thus, one of more aspects of the present disclosure may be implemented according to one or more of the following clauses.

Clause 1. A hemorrhoid bander, comprising: a housing; an actuation system positioned within the housing; a power source positioned within the housing, the power source configured to provide power to the actuation system; an outer shaft defining a hollow passageway; and an inner shaft positioned within the hollow passageway of the outer shaft, the inner shaft including a distal end having an opening, a hollow passageway, and a proximal end; wherein the inner shaft and the outer shaft are relatively movable between a first relative position and a second relative position; and wherein the actuation system is coupled to a proximal end of a first one of the inner shaft or the outer shaft and configured to change the inner shaft and the outer shaft between the first relative position and the second relative position, and a second one of the inner shaft and the outer shaft is fixedly coupled to the housing.

Clause 2. The hemorrhoid bander of clause 1, wherein the actuation system is coupled to the inner shaft and configured to retract the inner shaft.

Clause 3. The hemorrhoid bander of clause 2, wherein a rubber band is positioned on the distal end of the inner shaft, and wherein retraction of the inner shaft causes the outer shaft to push the rubber band off of the distal end of the inner shaft.

Clause 4. The hemorrhoid bander of any one of the preceding clauses, wherein the actuation system is coupled to the outer shaft and configured to extend the outer shaft.

Clause 5. The hemorrhoid bander of any one of the preceding clauses, further comprising a controller positioned within the housing, the controller configured to command the actuation system to retract the inner shaft a first predefined distance or extend the outer shaft a second predefined distance.

Clause 6. The hemorrhoid bander of any one of the preceding clauses, further comprising a pump positioned in the housing, and wherein the proximal end of the inner shaft is coupled to the pump such that the pump is in fluid communication with the hollow passageway and the opening of the inner shaft.

Clause 7. The hemorrhoid bander of clause 6, further comprising a controller positioned within the housing, wherein the controller is configured to: command the pump to operate, wherein operation of the pump is configured to produce a suction force sufficient to draw at least a portion of a hemorrhoid into the opening of the inner shaft; and command the actuation system to retract the inner shaft a predefined distance or to extend the outer shaft a predefined distance.

Clause 8. The hemorrhoid bander of any one of the preceding clauses, wherein the actuation system includes a motor and a drive train positioned within the housing, wherein the motor is movably coupled with the drive train, and wherein the drive train is movably coupled with the proximal end of the first one of the inner shaft or the outer shaft.

Clause 9. A hemorrhoid bander comprising: a housing; a pump positioned within the housing; an outer shaft coupled to the housing, the outer shaft defining a hollow passageway; and an inner shaft positioned within the hollow passageway of the outer shaft, wherein one of the inner shaft or the outer shaft is relatively movable, the inner shaft including a distal end having an opening, a hollow passageway, and a proximal end, wherein the proximal end of the inner shaft is coupled to the pump such that the pump is in fluid communication with the hollow passageway and the opening of the inner shaft.

Clause 10. The hemorrhoid bander of clause 9, wherein the pump is configured to provide a suction force sufficient to draw at least a portion of a hemorrhoid into the opening of the inner shaft.

Clause 11. The hemorrhoid bander of any one of clauses 9 and 10, further comprising a power source coupled to the pump and positioned within the housing.

Clause 12. The hemorrhoid bander of any one of clauses 9-11, further comprising an actuation system positioned within the housing, the actuation system powered by a power source positioned within the housing, and wherein a portion of the actuation system is coupled proximate the proximal end of the inner shaft or is coupled proximate the proximal end of the outer shaft, and the actuation system configured to change one of the inner shaft and the outer shaft between a first relative position and a second relative position.

Clause 13. The hemorrhoid bander of clause 12, further comprising a controller positioned within the housing, wherein the controller is configured to: command the pump to operate, wherein operation of the pump is configured to produce a suction force sufficient to draw at least a portion of a hemorrhoid into the opening of the inner shaft; and command the actuation system to retract the inner shaft a first predefined distance; or command the actuation system to extend the outer shaft a second predefined distance.

Clause 14. A method of operation of a hemorrhoid bander, comprising: commanding, by a controller, a pump positioned within a housing of the hemorrhoid bander to generate a suction force to pull a hemorrhoid into an opening in an inner shaft of the hemorrhoid bander; and commanding, by the controller, a powered actuation system positioned within the housing of the hemorrhoid bander to retract the inner shaft, such that an outer shaft of the hemorrhoid bander pushes a rubber band off of a distal end of the inner shaft and onto the hemorrhoid as the inner shaft is retracted; or commanding, by the controller, the powered actuation system to extend the outer shaft, such that the outer shaft of the hemorrhoid bander pushes the rubber band off of the distal end of the inner shaft and onto the hemorrhoid as the outer shaft is extended.

Clause 15. The method of clause 14, wherein the controller is configured to command the powered actuation system to retract the inner shaft or extend the outer shaft after commanding the pump to generate the suction force.

Clause 16. The method of any one of clauses 14 and 15, wherein the controller is configured to stop the powered actuation system after the inner shaft has been retracted a first predefined distance or the outer shaft has been extended a second predefined distance.

Clause 17. The method of any one of clauses 14-16, wherein the controller is configured to stop the pump after the inner shaft has been retracted a predefined distance or the outer shaft has been extended a predefined distance.

Clause 18. The method of any one of clauses 14-17, wherein the pump, the powered actuation system, and the controller are wholly contained within the housing of the hemorrhoid bander.

Clause 19. The method of any one of clauses 14-18, wherein the hemorrhoid bander can be used with one hand.

Clause 20. The method of any one of clauses 14-19, further comprising commanding the controller to initiate a hemorrhoid banding procedure, and wherein the controller conducts the hemorrhoid banding procedure without further intervention after the controller has been commanded to initiate the hemorrhoid banding procedure.

Clause 21. A controller, comprising: a processor; and a memory configured to store instructions; wherein the processor is configured to execute the instructions to: responsive to a user input, activate a pump positioned within a housing of a hemorrhoid bander to pull a hemorrhoid into an opening in an inner shaft of the hemorrhoid bander; and actuate a powered actuation system within the housing of the hemorrhoid bander to: retract the inner shaft such that an outer shaft of the hemorrhoid bander pushes a rubber band off of a distal end of the inner shaft and onto the hemorrhoid as the inner shaft is retracted; or extend the outer shaft such that the outer shaft of the hemorrhoid bander pushes the rubber band off of the distal end of the inner shaft and onto the hemorrhoid as the outer shaft is extended.

Clause 22. The controller of clause 21, wherein the processor is further configured to command the powered actuation system to retract the inner shaft or extend the outer shaft after commanding the pump to generate a suction force.

Clause 23. The controller of any one of clauses 20 and 21, wherein the processor is further configured to stop the powered actuation system after the inner shaft has been retracted a first predefined distance or the outer shaft has been extended a second predefined distance.

Clause 24. The controller of any one of clauses 20-23, wherein the processor is further configured to stop the pump after the inner shaft has been retracted the first predefined distance or the outer shaft has been extended the second predefined distance.

Clause 25. The controller of any one of clauses 20-24, wherein the controller is wholly contained within the housing of the hemorrhoid bander in addition to the pump, the powered actuation system, the processor, the memory, and a power supply configured to provide power to the pump.

Clause 26. The hemorrhoid bander of any one of claims 1-13, wherein the hemorrhoid bander is used with one hand.

Clause 27. The method of any one of claims 14-20, wherein the hemorrhoid bander is used with one hand.

Clause 28. The controller of any one of claims 21-25, wherein the hemorrhoid bander is used with one hand.

While the aspects described herein have been described in conjunction with the examples above, the skilled person will understand that various alternatives, modifications, variations, and improvements may be made in the procedure without departing from the spirit of this disclosure. Accordingly, the examples, as set forth above, are intended to be illustrative, not limiting.

What is claimed is:

1. A hemorrhoid bander, comprising:
a housing;
an actuation system positioned within the housing;
a power source positioned within the housing, the power source configured to provide power to the actuation system;
an outer shaft defining a hollow passageway; and
an inner shaft positioned within the hollow passageway of the outer shaft, the inner shaft including a distal end having an opening, a hollow passageway, and a proximal end, wherein a rubber band is positioned on the distal end of the inner shaft;
wherein the inner shaft and the outer shaft are relatively movable between a first relative position and a second relative position; and
wherein the actuation system is directly coupled to the proximal end of the inner shaft and configured to change the inner shaft and the outer shaft between the first relative position and the second relative position, and the outer shaft is fixedly coupled to the housing.

2. The hemorrhoid bander of claim 1, wherein the actuation system is configured to retract the inner shaft.

3. The hemorrhoid bander of claim 2, wherein retraction of the inner shaft causes the outer shaft to push the rubber band off of the distal end of the inner shaft.

4. The hemorrhoid bander of claim 1, further comprising a controller positioned within the housing, the controller configured to command the actuation system to retract the inner shaft a first predefined distance.

5. The hemorrhoid bander of claim 1, further comprising a pump positioned in the housing, and wherein the proximal end of the inner shaft is coupled to the pump such that the pump is in fluid communication with the hollow passageway and the opening of the inner shaft.

6. The hemorrhoid bander of claim 5, further comprising a controller positioned within the housing, wherein the controller is configured to:
command the pump to operate, wherein operation of the pump is configured to produce a suction force sufficient to draw at least a portion of a hemorrhoid into the opening of the inner shaft; and
command the actuation system to retract the inner shaft a predefined distance.

7. The hemorrhoid bander of claim 1, wherein the actuation system includes a motor and a drive train positioned within the housing, wherein the motor is movably coupled with the drive train, and wherein the drive train is movably coupled with the proximal end of the inner shaft.

8. A hemorrhoid bander comprising:
a housing;
a pump positioned within the housing;
a power source coupled to the pump and positioned within the housing,
an outer shaft fixedly coupled to the housing, the outer shaft defining a hollow passageway; and
an inner shaft positioned within the hollow passageway of the outer shaft, wherein the inner shaft is relatively movable, the inner shaft including a distal end having an opening, a hollow passageway, and a proximal end, wherein the proximal end of the inner shaft is coupled to the pump such that the pump is in fluid communication with the hollow passageway and the opening of the inner shaft, wherein the proximal end of the inner shaft is positioned within the housing, and wherein a rubber band is positioned on the distal end of the inner shaft.

9. The hemorrhoid bander of claim 8, wherein the pump is configured to provide a suction force sufficient to draw at least a portion of a hemorrhoid into the opening of the inner shaft.

10. The hemorrhoid bander of claim 8, further comprising an actuation system positioned within the housing, the actuation system powered by the power source positioned within the housing, and wherein a portion of the actuation system is coupled proximate the proximal end of the inner shaft, and the actuation system configured to change the inner shaft between a first relative position and a second relative position.

11. The hemorrhoid bander of claim 10, further comprising a controller positioned within the housing, wherein the controller is configured to:
command the pump to operate, wherein operation of the pump is configured to produce a suction force sufficient to draw at least a portion of a hemorrhoid into the opening of the inner shaft; and command the actuation system to retract the inner shaft a first predefined distance.

12. A method of operation of the hemorrhoid bander of claim 1, comprising:
commanding, by a controller, a pump positioned within the housing of the hemorrhoid bander to generate a suction force to pull a hemorrhoid into the opening of the inner shaft of the hemorrhoid bander; and
commanding, by the controller, the actuation system to retract the inner shaft, such that the outer shaft of the hemorrhoid bander pushes the rubber band off of the distal end of the inner shaft and onto the hemorrhoid as the inner shaft is retracted.

13. The method of claim 12, wherein the controller is configured to command the actuation system to retract the inner shaft after commanding the pump to generate the suction force.

14. The method of claim 13, wherein the controller is configured to stop the pump after the inner shaft has been retracted a first predefined distance.

15. The method of claim 12, wherein the controller is configured to stop the actuation system after the inner shaft has been retracted a first predefined distance.

16. The method of claim 12, wherein the pump, the actuation system, and the controller are wholly contained within the housing of the hemorrhoid bander.

17. The method of claim 12, further comprising commanding the controller to initiate a hemorrhoid banding procedure, and wherein the controller conducts the hemorrhoid banding procedure without further intervention after the controller has been commanded to initiate the hemorrhoid banding procedure.

18. A controller, comprising:
a processor; and
a memory configured to store instructions;
wherein the processor is configured to execute the instructions to:
responsive to a user input, activate a pump positioned within a housing of a hemorrhoid bander to pull a hemorrhoid into an opening in an inner shaft of the hemorrhoid bander; and
actuate a powered actuation system within the housing of the hemorrhoid bander to:
retract the inner shaft such that an outer shaft of the hemorrhoid bander pushes a rubber band off of a distal end of the inner shaft and onto the hemorrhoid as the inner shaft is retracted, wherein the inner shaft is directly coupled to the powered actuation system and wherein the outer shaft is fixedly coupled to the housing.

19. The controller of claim 18, wherein the processor is further configured to command the powered actuation system to retract the inner shaft after commanding the pump to generate a suction force.

20. The controller of claim 18, wherein the processor is further configured to stop the powered actuation system after the inner shaft has been retracted a first predefined distance.

21. The controller of claim 20, wherein the processor is further configured to stop the pump after the inner shaft has been retracted the first predefined distance.

22. The controller of claim 18, wherein the controller is wholly contained within the housing of the hemorrhoid bander in addition to the pump, the powered actuation system, the processor, the memory, and a power supply configured to provide power to the pump.

23. The controller of claim 18, wherein the controller is configured to carry out a ligation process of the hemorrhoid bander without further intervention from a user after the user input has been provided.

24. The controller of claim 18, wherein the processor is configured to stop the pump and the powered actuation system after a predefined time period has elapsed.

* * * * *